(12) United States Patent
Bak et al.

(10) Patent No.: US 10,813,322 B1
(45) Date of Patent: Oct. 27, 2020

(54) *DIONAEA* PLANT 'FLEXX'

(71) Applicant: Corn Bak BV, Assendelft (NL)

(72) Inventors: Elly Bak, Rijsenhout (NL); Nicolaas Steur, Oude Niedorp (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 16/436,131

(22) Filed: Jun. 10, 2019

(51) Int. Cl.
*A01H 5/10* (2018.01)
*A01H 6/30* (2018.01)

(52) U.S. Cl.
CPC ............... *A01H 6/30* (2018.05); *A01H 5/10* (2013.01)

(58) Field of Classification Search
CPC ...................................................... A01H 5/12
See application file for complete search history.

(56) References Cited

PUBLICATIONS

Venus Fly Trap Registered Cultivars List flytrapcare.com/venus-fly-trap-cultivated-variety-list (web page) (Year: 2018).*

* cited by examiner

*Primary Examiner* — David H Kruse
(74) *Attorney, Agent, or Firm* — Cassandra Bright

(57) ABSTRACT

A new and distinct *Dionea* cultivar named 'FLEXX' characterized by its small plant size, measuring about 3 to 10 cm high at maturity. Plants are well-filled in and full, producing a large quantity of long-lasting traps having a unique red-purple interior color.

5 Claims, 1 Drawing Sheet
(1 of 1 Drawing Sheet(s) Filed in Color)

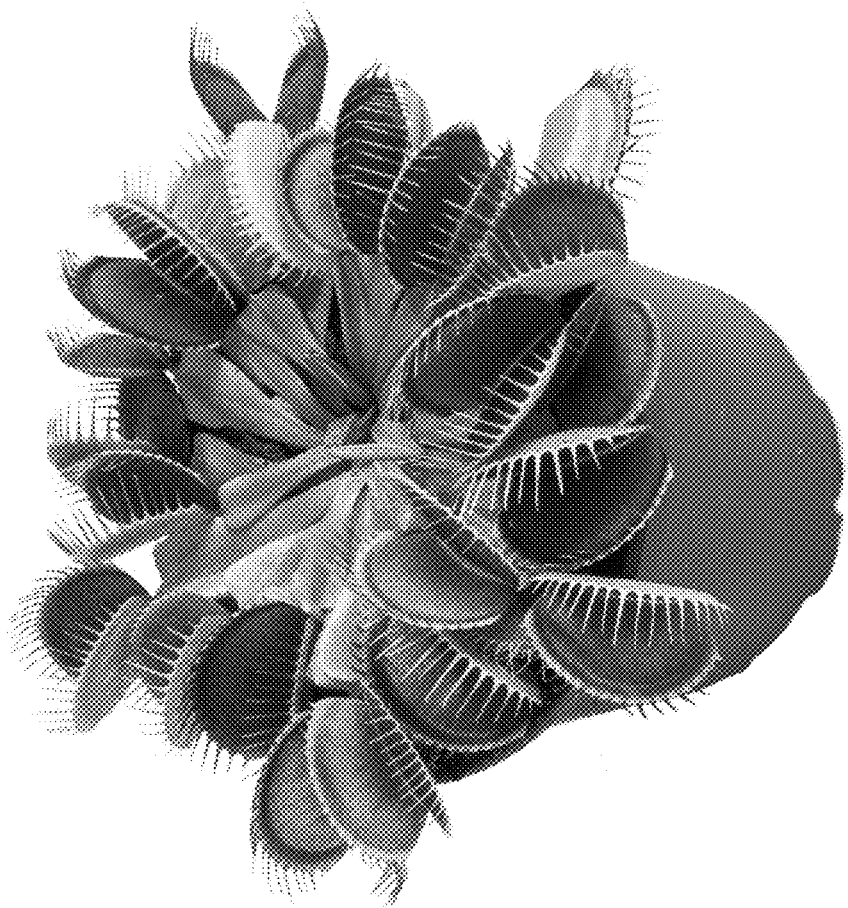

*DIONAEA* PLANT 'FLEXX'

FIELD OF THE INVENTION

The present invention relates to a new, distinct and stable cultivar of *Dionaea*, hereinafter referred to as 'FLEXX'. The present invention relates to seeds which are the *Dionaea* 'FLEXX', as well as, plants and plant parts produced by these seeds which have all of the morphological and physiological characteristics of the *Dionaea* cultivar 'FLEXX'. The present invention also relates to methods for producing these seeds and plants of the *Dionaea* cultivar 'FLEXX'. Furthermore, the present invention relates to a method of producing progeny *Dionaea* plants by crossing *Dionaea* 'FLEXX', as either the female or seed or male or pollen parent, with another *Dionaea* plant and selecting progeny.

BACKGROUND OF THE INVENTION

The present invention relates to a new, distinct and stable cultivar, botanically known as *Dionaea muscipula*, and hereinafter referred to by the variety denomination 'FLEXX'. The new *Dionaea* 'FLEXX' originated from a familial cross of unnamed proprietary seedlings. Development of the parent varieties was conducted over several years, as part of a controlled breeding program by the inventors. The cross resulting in the new variety 'FLEXX' was made during 2014. 'FLEXX' first flowered in 2015, in Assendelft, The Netherlands. The objective of the breeding program is to create new *Dionaea* plants with interesting characteristics for the ornamental market. Characteristics sought included a high quantity of long-lasting traps in interesting colors on a small plant.

*Dionaea* is a member of the Droseraceae family. *Dionaea muscipula* is the only species of the genus *Dionaea* and known under the common name Venus flytrap. It is native to the subtropical wetlands on the East Coast of the United States in North Carolina and South Carolina. The Venus flytrap is the most famous carnivorous plant and consists of a small rosette of leaves, each of which end in a trap edged with pointed teeth.

The Venus flytrap is a plant exhibiting visible movement, whose trap is triggered when one of the internal trigger hairs is touched twice or when two hairs of the same leaf are touched. There is considerable variation in the coloration of *Dionaea* traps. Most trap interiors are varying degrees of bright red, with the pigment largely deposited in the glands. Newly emerged traps are usually lighter until exposed to light for a period. However, there are a few plants where red pigment is never present, with the trap interiors remaining yellowish green even in full light. There are also variations in petiole shape and width and whether the leaf lies flat on the ground or extends up at an angle of about 45-60°.

Most commonly the Venus flytrap develops flower stalks in May or June. As dormancy approaches at the end of the season, most leaves will turn black and dry. Normally growth ceases during the dormancy period. For detailed information regarding *Dionaea* morphology and cultivation, reference is made to the following publications, which are incorporated herein by reference: Reference: Schnell, Donald E., CARNIVOROUS PLANTS OF THE UNITED STATES AND CANADA, Timber Press, Inc., (2002); Lecoufle, Marcel., CARNIVOROUS PLANTS CARE AND CULTIVATION, Cassell Publishers Limited (1990).

*Dionaea* are popular commercial novelty ornamental plants. A need exists for a greater variety of *Dionaea* cultivars with consistent, attractive and unique ornamental features. Additionally, a need exists for additional *Dionaea* cultivars that can be easily propagated by seed, and reproduce the desired features consistently.

The new *Dionaea* 'FLEXX' was developed through a controlled breeding program and exhibits unique, desirable and stable characteristics.

SUMMARY OF THE INVENTION

The present invention provides *Dionaea* plant selections that are a solid, small-sized, cultivar with long-lasting traps having a red-purple interior trap color.

These and other objectives have been achieved in accordance with the present invention which provides 'FLEXX' as a new *Dionaea* cultivar that is a product of a planned breeding program conducted by the inventors, Elly Bak and Nico D. M. Steur, in Assendelft, The Netherlands. The cross resulting in the new cultivar 'FLEXX' is a familial cross of proprietary seedlings which have a sufficient degree of homozygosity such that the progeny of the cross are genotypically and phenotypically uniform. The new cultivar 'FLEXX' therefore can be produced by sexual reproduction by crossing the parental to produce a population of progeny plants, each of which has the combination of characteristics as herein disclosed for the new variety 'FLEXX'.

Seeds which are the cultivar 'FLEXX' are produced by crossing the parental selections and have been deposited with the NCIMB limited, Ferguson Building, Craibstone Estate, Bucksburn, Aberdeen, AB21 9YA, United Kingdom. Accession No. NCIMB-43424 has been designated.

OBJECTS OF THE INVENTION

The present invention relates to seeds which produce *Dionaea* 'FLEXX'. The present invention also relates to *Dionaea* plants, and parts thereof, having all the physiological and morphological characteristics of *Dionaea* 'FLEXX'. The present invention relates to a plant produced from seeds which are *Dionaea* 'FLEXX'. The present invention also relates to plant parts, such as pollen, seeds or inflorescence produced by *Dionaea* 'FLEXX'.

The present invention relates to a method of producing seed which are *Dionaea* 'FLEXX', by a crossing the unpatented proprietary parent selections of *Dionaea muscipula* and harvesting seeds produced from said cross.

The present invention also relates to a method of producing plants having all the physiological and morphological characteristics of the *Dionaea* 'FLEXX' comprising the steps of (a) crossing the proprietary parent selections of *Dionaea muscipula* (unpatented). (b) harvesting seeds produced from said cross; and (c) producing plants from said harvested seeds.

BRIEF DESCRIPTION OF THE INVENTION

The following traits have been repeatedly observed and are determined to be unique characteristics of 'FLEXX' which in combination distinguish this *Dionaea* as a new and distinct cultivar:
1. Well filled in, full plant growth habit
2. Small rosette plant, measuring about 3 to 10 cm in height (above the pot at maturity);
3. Mature trap lobes have unique red-purple interior color.
4. Well-suited for smaller pot sizes
5. Long-lasting habit.

The new *Dionaea* 'FLEXX' can be compared to the unpatented commercial variety *Dionaea* 'Big Mouth'. Plants of the new cultivar 'FLEXX' are similar to plants of *Dionaea* a 'Big Mouth' in most horticultural characteristics, however the varieties differ in the following:
1. *Dionaea* 'Big Mouth' has shorter petioles
2. Interior surface color of trap lobes of this comparator is a different shade of red
3. This comparator's exterior surface color of trap lobes is yellow.

The new *Dionaea* 'FLEXX' can also be compared to the unpatented commercial variety *Dionaea* 'Red Green'. Plants of the new cultivar 'FLEXX' differ from plants of *Dionaea* 'Red Green' in the following characteristics:
1. *Dionaea* 'Red Green' has longer petioles.
2. *Dionaea* 'Red Green' has smaller sized traps
3. *Dionaea* 'Red Green' is a less vigorous plant 'FLEXX' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant.

BRIEF DESCRIPTION OF THE PHOTOGRAPH

The patent or application file contains at least one drawing executed in color. Copies of this patent or patent application publication with color drawings will be provided by the Office upon request and payment of the necessary fees.

The accompanying photograph illustrates the overall appearance of the new *Dionaea* cultivar 'FLEXX' showing the colors as true as is reasonably possible with colored reproductions of this type. Colors in the photograph may differ slightly from the color values cited in the detailed botanical description which accurately describes the color of 'FLEXX'.

The accompanying drawing shows an overhead view perspective of a typical potted plant of 'FLEXX', at approximately 9 months of age from potting size.

Detailed Botanical Description

The present invention was created by the inventors, Elly Bak and Nicolaas D. M. Steur in 2014 and flowered for the first time in 2015 in Assendelft, The Netherlands.

This invention is directed to *Dionaea* plant having all the morphological and physiological characteristics of the cultivar 'FLEXX' produced from seeds which are the product of the cross of the proprietary parental selections of *Dionaea muscipula* Both parents have a sufficient degree of homozygosity such that the progeny of the cross were, and continue to be, phenotypically uniform. The new cultivar 'FLEXX' can therefore be produced by sexual reproduction by crossing of the parental *Dionaea muscipula* selections to produce a population of progeny plants, each of which has the combination of characteristics herein disclosed for the new cultivar 'FLEXX'.

The new cultivar 'FLEXX' can also be produced by asexually reproducing progeny from the cross of the parental selections. Asexual reproduction of the new cultivar by vegetative means by cuttings was first performed in 2016 in Assendelft, The Netherlands. The first 'FLEXX' plants propagated through the use of leaf cuttings flowered in 2017 in Assendelft, The Netherlands, and have demonstrated that the new cultivar reproduces true-to-type and that the combination of characteristics as herein disclosed for the new cultivar are firmly fixed and retained through successive generations of asexual reproduction.

The aforementioned photograph, together with the following observations, measurements and values describe the new *Dionaea muscipula* 'FLEXX' as grown in a greenhouse in Assendelft, The Netherlands, under conditions which closely approximate those generally used in commercial practice. Plants of 'FLEXX' were grown in a greenhouse with day temperatures ranging from 20° C. to 28° C. and night temperatures ranging from 18° C. to 23° C. No artificial lighting or photoperiodic treatments were conducted.

Color references are made to the Royal Horticultural Society Color Chart (RHS), 2001 edition, except where general colors of ordinary significance are used. Color values were taken under daylight conditions in a greenhouse in Assendelft, The Netherlands. The age of the plants of 'FLEXX' described is about 20 weeks of age.

Classification

Botanical: *Dionaea muscipula*.
  Plant
  General Appearance and Form: Tender herbaceous plant composed of ornamental traps.
  Height: Approx. 3 to 10 cm (above the soil line at maturity)
  Width: About 12 cm
  Shape: Rosette
  Growth habit: Upright and outwardly arching growth habit. Rosette leaves are erect
  when young, becoming outwardly arching with development.
  Plant Vigor: Good
  Flowering Season: A fully grown plant can flower year round, starting 10 weeks after induction of natural light or through flowering treatment.
  Cold Tolerance: Frost tender. Temperatures below 5° C. may damage plants.
  Fragrance: None observed.
  Foliage
  Arrangement: Rosette
  Size of leaf:
    length: Average 4.5 cm (without trap)
    width: Average range 0.5-2 cm (without trap)
  Shape of leaf: spatulate
  Color:
    Upperside: Near RHS Yellow-Green 144A
    Underside: Near RHS Yellow-Green 144A
  Quantity: Average 22
Petiole:
  Length: Approx. 1 mm
  Diameter: Approx. 1 mm
  Color: Near RHS Yellow-Green 144A
  Texture: Smooth
  Traps
  Size of trap:
    Length: About 2.5 cm from leaf attachment
    Width: About 1.5 cm closed. 2.5 to 3.0 cm open
  Shape of trap: Lobate
  Margin: Ciliate
  Color:
    Outside: Near RHS Yellow-Green 144A
    Inside: Background color near RHS Yellow-Green 144A, completely overlayed with Red-purple RHS 59B
Quantity: Average 22

Trigger hairs:
  Length: 2 mm
  Color: Orange-White, closest to RHS 159B
Guard Hairs:
  Length: Average range 2 to 8 mm (largest occurring at trap mid-section)
  Color: Near RHS Yellow-Green 144D
Digestive gland: Not visible.
Nectar Gland: Not visible.
Exterior trap vein color: Near RHS Yellow-Green 144A
Interior trap vein color: Near RHS Greyed-Purple183B
  Flowers
Quantity: 2 to 4
Length of flowering stem: approx. 20 cm
Color: Near RHS Yellow-Green 144A, base Red-Purple 59B
Inflorescence type: Umbel composed of on average 8 flowers.
Diameter of individual flower: Approx. 2.5 cm
Color of flower: Near RHS White 155A
  Reproductive Organs:
  SEEDS/FRUIT: Fruit and seed production have not been observed on plants of *Dionaea* 'FLEXX'.
  DISEASE/PEST RESISTANCE: Not observed to date.
  DISEASE/PEST SUSCEPTIBILITY: Not observed to date.

We claim:

1. A *Dionaea* plant named 'FLEXX', representative seed having been deposited at the NCIMB in Aberdeen, Scotland NCIMB accession number 43424.

2. A *Dionaea* seed that produces the *Dionaea* plant of claim 1.

3. A plant part obtained from the *Dionaea* plant of claim 1.

4. A method of producing *Dionaea* progeny plant comprising the steps of
  (a) crossing *Dionaea* 'FLEXX', wherein a representative sample of seed of *Dionaea* 'FLEXX' has been deposited under NCIMB accession number 43424, produced from seed as a female or male parent with another *Dionaea* plant, and
  (b) selecting progeny.

5. The method according to claim 4, wherein the second *Dionaea* plant is 'FLEXX', wherein a representative sample of seed of said *Dionaea* 'FLEXX' has been deposited under NCIMB accession number 43424.

* * * * *